(12) United States Patent
Nagi et al.

(10) Patent No.: US 8,791,109 B2
(45) Date of Patent: *Jul. 29, 2014

(54) COMPOSITIONS CONTAINING MICRONIZED TANAPROGET PREPARED BY WET GRANULATION

(71) Applicant: Wyeth LLC, Madison, NJ (US)

(72) Inventors: Arwinder S. Nagi, Moorpark, CA (US); Ramarao S. Chatlapalli, Hopewell Junction, NY (US); Shamim Hasan, East Elmhurst, NY (US); Rolland W. Carson, Middletown, NY (US); Mohamed Ghorab, West Lafayette, IN (US)

(73) Assignee: Wyeth LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,177

(22) Filed: Nov. 29, 2012

(65) Prior Publication Data

US 2013/0142838 A1 Jun. 6, 2013

Related U.S. Application Data

(63) Continuation of application No. 11/412,014, filed on Apr. 26, 2006, now Pat. No. 8,343,965.

(60) Provisional application No. 60/675,599, filed on Apr. 28, 2005.

(51) Int. Cl.
*A61K 31/535* (2006.01)

(52) U.S. Cl.
USPC ............. 514/230.5; 514/170; 544/70; 544/92

(58) Field of Classification Search
USPC ........................... 514/170, 230.5; 544/70, 92
See application file for complete search history.

(56) References Cited

U.S. PATENT DOCUMENTS

| | | | |
|---|---|---|---|
| 6,436,929 | B1 | 8/2002 | Zhang |
| 7,268,149 | B2 | 9/2007 | Fensome |
| 7,317,037 | B2 | 1/2008 | Fensome |
| 7,496,489 | B2 | 2/2009 | Olland |
| 7,514,466 | B2 | 4/2009 | Wilk |
| 7,569,679 | B2 | 8/2009 | Shen |
| 7,582,755 | B2 | 9/2009 | Wilk |
| 7,759,341 | B2 | 7/2010 | Tesconi |
| 7,767,668 | B2 | 8/2010 | Nagi |
| 7,786,297 | B2 | 8/2010 | Chatlapalli |
| 7,968,709 | B2 | 6/2011 | Tesconi |
| 8,114,869 | B2 | 2/2012 | Tesconi |
| 8,343,965 | B2 | 1/2013 | Nagi |
| 2003/0092711 | A1 | 5/2003 | Zhang |
| 2003/0119796 | A1 | 6/2003 | Strony |
| 2004/0006060 | A1 | 1/2004 | Fensome |
| 2004/0014798 | A1 | 1/2004 | Fensome |
| 2004/0127476 | A1 | 7/2004 | Kershman |
| 2004/0265355 | A1 | 12/2004 | Shalaby |
| 2006/0009428 | A1 | 1/2006 | Grubb |
| 2006/0030615 | A1 | 2/2006 | Fensome |
| 2006/0035843 | A1 | 2/2006 | Shen |
| 2006/0142280 | A1 | 6/2006 | Zhang |
| 2006/0246128 | A1 | 11/2006 | Nagi |
| 2006/0246135 | A1 | 11/2006 | Nagi |
| 2006/0247235 | A1 | 11/2006 | Tesconi |
| 2006/0247236 | A1 | 11/2006 | Chatlapalli |
| 2006/0280800 | A1 | 12/2006 | Nagi |
| 2010/0189789 | A1 | 7/2010 | Nagi |
| 2010/0292198 | A1 | 11/2010 | Grubb |
| 2011/0091539 | A1 | 4/2011 | Nagi |
| 2012/0114748 | A1 | 5/2012 | Nagi |
| 2012/0115858 | A1 | 5/2012 | Tesconi |

FOREIGN PATENT DOCUMENTS

| | | |
|---|---|---|
| JP | 2002-543192 | 12/2002 |
| JP | 2005-535624 | 11/2005 |
| JP | 2005-535628 | 11/2005 |
| JP | 2007-534760 | 11/2007 |
| JP | 2007-534767 | 11/2007 |
| JP | 2008-505909 | 2/2008 |
| JP | 2008-509216 | 3/2008 |
| JP | 2008-509217 | 3/2008 |
| JP | 2008-509917 | 4/2008 |
| JP | 2008-510722 | 4/2008 |
| JP | 2008-539254 | 11/2008 |
| JP | 2008-539256 | 11/2008 |
| JP | 2008-539258 | 11/2008 |
| JP | 2008-539262 | 11/2008 |
| WO | WO-95/05807 | 3/1995 |
| WO | WO-04/000801 | 12/2003 |
| WO | WO-2006/014476 | 2/2006 |
| WO | WO-2006/116596 | 11/2006 |

OTHER PUBLICATIONS

English translation of an Office Action dated Nov. 26, 2013 and issued in related Japanese Patent Application No. 2012-169806.

(Continued)

*Primary Examiner* — Ali Soroush

(74) *Attorney, Agent, or Firm* — Howson & Howson LLP

(57) ABSTRACT

Compositions, preferably pharmaceutical compositions, containing micronized tanaproget, or pharmaceutically acceptable salt thereof, microcrystalline cellulose, croscarmellose sodium, sodium lauryl sulfate, butylated hydroxyanisole, povidone, and magnesium stearate, are provided. The compositions are useful in contraception and hormone replacement therapy and in the treatment and/or prevention of uterine myometrial fibroids, benign prostatic hypertrophy, benign and malignant neoplastic to disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors, and in the preparation of medicaments useful therefor. Additional uses include stimulation of food intake.

29 Claims, No Drawings

(56) References Cited

OTHER PUBLICATIONS

Fensome, "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonists Tanaproget" J. Med. Chem., 48:5092-5095 (Jul. 12, 2005).
Zhang, "Novel 6-Aryl-1,4-dihydrobenzo[d][1,3]oxazine-2-thiones as Potent, Selective, and Orally Active Nonsteroidal Progesterone Receptor Agonists", Bioorg. & Med. Chem. Lett., 13:1313-1316 (Apr. 7, 2003).
Winneker, "Nonsteroidal Progesterone Receptor Modulators: Structure Activity Relationships" Seminars in Reproductive Medicine, 23(1):46 (Feb. 2005).
Prous, "Annual Update 2003/2004—Treatment of Endocrine Disorders", Drugs of the Future, vol. 29, No. 11, pp. 86-87, (2004).
Bapst, "Clinical Pharmacokinetics of Tanaproget, A Non-Steroidal Progesterone Receptor (PR) Agonist, in Healthy Cycling Women During 28 Days of Administration", American Society for Clinical Pharmacology and Therapeutics, Abstract PI-138, (Feb. 2005), p. 44.
Crabtree, "Development of a Mouse Model of Mammary Gland Versus Uterus Tissue Selectivity Using Estrogen- and Progesterone-Regulated Gene Markers", Journal of Steroid Biochemistry & Molecular Biology, vol. 101, (Sep. 2006; e-published Aug. 22, 2006), pp. 11-21.
Bapst, "Pharmacokinetics and Safety of Tanaproget, a Nonsteroidal Progesterone Receptor Agonist, in Healthy Women", Contraception, vol. 74 (Nov. 2006; e-published Sep. 15, 2006), pp. 414-418.
Bruner-Tran, "Down-Regulation of Endometrial Matrix Metalloproteinase-3 and -7 Expression in Vitro and Therapeutic Regression of Experimental Endometriosis in Vivo by a Novel Nonsteroidal Progesterone Receptor Agonist, Tanaproget", The Journal of Clinical Endocrinology & Metabolism, vol. 91, No. 4 (Apr. 2006; e-published Jan. 17, 2006), pp. 1554-1560.
Mitsuru, "Keiko-Toyo-Seizai no Sekkyei to Hyoka", Yakugyo Jiho, Inc., pp. 81-85, Japan (1995).
Japan Pharmaceutical Excipients Council Ed., "Iyakuhin-Tenkabutsu Jiten", Yakuji Nippo Limited, pp. 17, 46, 49, 72, 82, 124, 133, 144, and 214, Japan (Jan. 14, 1994).
Search Report dated Jun. 12, 2007 and issued in International Patent Application No. PCT/US2006/016025.
Office Action dated Dec. 17, 2009 and issued in U.S. Appl. No. 11/412,022.
Applicant's Response to the Office Action dated Dec. 17, 2009 and issued in U.S. Appl. No. 11/412,022.
Office Action dated Jul. 22, 2010 issued in U.S. Appl. No. 11/412,022.
Office Action dated Oct. 1, 2008 and issued in U.S. Appl. No. 11/411,523.
Applicant's Response to the Office Action dated Oct. 1, 2008 and issued in U.S. Appl. No. 11/411,523.
Office Action dated Mar. 4, 2009 and issued in U.S. Appl. No. 11/411,523.
Applicant's Response to the Office Action dated Mar. 4, 2009 and issued in U.S. Appl. No. 11/411,523.
Notice of Allowance dated Jan. 4, 2010 and issued in U.S. Appl. No. 11/411,523.
Office Action dated Jul. 13, 2010 and issued in U.S. Appl. No. 11/448,965.
Applicant's Response to the Office Action dated Jul. 13, 2010 and issued in U.S. Appl. No. 11/448,965.
Office Action dated Jan. 28, 2011 and issued in U.S. Appl. No. 11/448,965.
Applicant's Response to the Office Action dated Jan. 28, 2011 and issued in U.S. Appl. No. 11/448,965.
Office Action dated Mar. 12, 2009 issued in U.S. Appl. No. 11/174,592.
Applicant's Response to the Office Action dated Mar. 12, 2009 issued in U.S. Appl. No. 11/174,592.
Office Action dated Nov. 5, 2009 issued in U.S. Appl. No. 11/174,592.
Office Action dated Dec. 16, 2011 issued in U.S. Appl. No. 12/772,280.
Applicant's Response to the Office Action dated Dec. 16, 2011 issued in U.S. Appl. No. 12/772,280.
Office Action dated Mar. 23, 2012 issued in U.S. Appl. No. 12/772,280.
Office Action dated Sep. 18, 2012 and issued in U.S. Appl. No. 12/752,520.
Applicant's Response to the Office Action dated Sep. 18, 2012 and issued in U.S. Appl. No. 12/752,520.
Office Action dated Oct. 3, 2012 and issued in U.S. Appl. No. 12/975,444.
Applicant's Response to the Office Action dated Oct. 3, 2012 and issued in U.S. Appl. No. 12/975,444.
Office Action dated Mar. 17, 2010 and issued in Mexican Patent Application No. MX/A/2007/013468.
Agent's informal English translation of the Office Action dated Mar. 17, 2010 and issued in Mexican Patent Application No. MX/A/2007/013468.
Applicant's instructions to the agent regarding responding to the Office Action dated Mar. 17, 2010 and issued in Mexican Patent Application No. MX/A/2007/013468.
English translation of the Office Action dated Jul. 31, 2009 and issued in Chinese Patent Application No. 200680014222.2.
Applicant's instructions to the agent regarding responding to the Office Action dated Jul. 31, 2009 and issued in Chinese Patent Application No. 200680014222.2.
English translation of an Office Action dated Nov. 3, 2010 and issued in Chinese Patent Application No. 200680014222.2.
English translation of an Office Action dated Apr. 16, 2012 and issued in corresponding Chinese Patent Application No. 200680014222.2.
English translation of an Office Action dated Jan. 31, 2012 and issued in corresponding Japanese Patent Application No. 2008-509120.
Office Action dated Feb. 27, 2012 and issued in corresponding Indian Patent Application No. 4108/KOLNP/07.
Applicant's Response to the Office Action dated Feb. 27, 2012 and issued in corresponding Indian Patent Application No. 4108/KOLNP/07.

COMPOSITIONS CONTAINING MICRONIZED TANAPROGET PREPARED BY WET GRANULATION

BACKGROUND OF THE INVENTION

Micronized tanaproget and compositions containing the same are provided.

Intracellular receptors (IR) form a class of structurally related gene regulators known as "ligand dependent transcription factors". The steroid receptor family is a subset of the IR family, including the progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the cell membrane via passive diffusion, and binds to the IR to create a receptor/ligand complex. This complex binds to specific gene promoters present in the cell's DNA. Once bound to the DNA, the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control compositions, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Tanaproget, 5-(4,4-dimethyl-2-thioxo-1,4-dihydro-2H-3,1-benzoazin-6-yl)-1-methyl-1H-pyrrole-2-carbonitrile, is a progesterone receptor modulator and is effective in contraception, hormone replacement therapy, and treating carcinomas and adenocarcinomas, dysfunctional bleeding, uterine leiomyomata, endometriosis, and polycystic ovary syndrome.

What is needed in the art are compositions containing tanaproget for administration to a mammalian subject.

SUMMARY OF THE INVENTION

In one aspect, a composition containing micronized tanaproget, microcrystalline cellulose, croscarmellose sodium, sodium lauryl sulfate, povidone, magnesium stearate, and butylated hydroxyanisole is provided.

In another aspect, a process for preparing compositions containing micronized tanaproget is provided.

In a further aspect, kits including a composition containing micronized tanaproget are provided.

Other aspects and advantages are described further in the following detailed description of the preferred embodiments thereof.

DETAILED DESCRIPTION OF THE INVENTION

Effective pharmaceutical compositions containing micronized tanaproget are provided. The micronized tanaproget can be readily formulated into an oral dosage unit, and is particularly well suited for a directly compressible unit. The inventors have found that tablets or caplets prepared by direct compression of or capsules containing the micronized tanaproget compositions of the invention exhibited rapid and complete drug release, as compared to nonmicronized tanaproget. Thus, the compositions of the invention provide for fast drug release.

Briefly, tanaproget is micronized, in one embodiment under nitrogen and by means of conventional micronizing techniques, for example with a Trost or jet mill, applied to non-micronized tanaproget. One method of preparation of non-micronized tanaproget is described in U.S. Pat. No. 6,436,929, and generally in US Patent Application Publication No. 2005/0272702, published Dec. 8, 2005. However, the invention is not limited to the method by which the non-micronized tanaproget is produced.

In another embodiment, non-micronized tanaproget is purified by recrystallization. In one embodiment, the tanaproget is recrystallized from acetone and water. In a further embodiment, the tanaproget is dissolved in acetone, the acetone solution heated, water added to the heated acetone solution, and the acetone/water solution cooled to provide purified tanaproget. This purification specifically includes dissolving crude tanaproget in acetone and heating the solution to about 45 to about 51° C. After circulating the heated solution through a carbon filter for at leas about 4 hours, the filtered solution was concentrated using procedures known to those of skill in the art. After adding water to the concentrated solution, in one embodiment at a rate which does not cool the refluxing acetone solution, the acetone/water solution was cooled to about −6 to about 0° C. In one embodiment, the acetone/water solution was cooled at a rate of less than about 0.5° C./minute. After holding the batch at the reduced temperature for at least about 3 hours, the precipitated, purified tanaproget is collected using filtration. The collected solid is washed with a water/acetone mixture, in one embodiment washed twice with a 1:1 water/acetone mixture. The washed purified tanaproget was then dried at less than 35° C. for about 4 hours. Further drying at less than about 50° C. was performed to remove residual acetone/water as measured by spectroscopic methods.

In one embodiment, micronized tanaproget prepared for use has a particle size of less than about 20 μm, less than about 15 μm, or less than about 10 μm. In a further embodiment, 90% of the particles were less than or equal to about 20 μm and 50% were less than or equal to about 15 μm or about 10 μm as determined by the Malvern method, which is readily understood by one of skill in the art.

The micronized tanaproget encompasses tautomeric forms of tanaproget and salts derived from pharmaceutically or physiologically acceptable acids, bases, alkali metals and alkaline earth metals. Also included are derivatives of tanaproget, including, but not limited to, esters, carbamates, sulfates, ethers, oximes, carbonates, and the like.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates.

These salts, as well as the nonmicronized and micronized tanaproget can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Micronized tanaproget discussed herein also encompasses "metabolites" which are unique products formed by processing tanaproget by the cell or patient. In one embodiment, metabolites are formed in vivo.

In one embodiment, the compositions of the invention were prepared by wet mixing micronized tanaproget, based upon the total weight of the unit dose, with the other components of the composition.

As referred to herein below, the term "wt/wt" refers to the weight of one component based on the total weight of the composition. In one embodiment, this ratio does not include the weight of the capsule, the weight of any filler utilized in the capsule, and seal coating, if so utilized.

A. Compositions

The compositions are formulated to provide rapid release of tanaproget, while simultaneously being stable under conditions of storage. In one embodiment, the composition contains micronized tanaproget, or a pharmaceutically acceptable salt thereof, microcrystalline cellulose (MCC), croscarmellose sodium, sodium lauryl sulfate (SLS), povidone, magnesium stearate, and butylated hydroxyl anisole (BHA), also known as butylated hydroxyanisole.

In one embodiment, micronized tanaproget is present in the composition of the invention in an amount from 0.01% wt/wt to 25% wt/wt of the composition. This amount may be varied, depending upon the amount of micronized tanaproget to be delivered to a patient. In another embodiment, an overage of tanaproget is utilized, e.g., a 5% overage.

The desired therapeutic regimen can be taken into consideration when formulating a composition of the invention. In one example, micronized tanaproget is present in the formulation at about 0.01% wt/wt, based upon the total weight of the unit dose. In a further example, micronized tanaproget is present in the formulation at about 0.10% wt/wt based upon the total weight of the unit dose. In another example, micronized tanaproget is present in the composition at about 1% wt/wt based upon the total weight of the unit dose. In a further example, micronized tanaproget is present in the composition at about 5% wt/wt based upon the total weight of the unit dose. In yet another example, micronized tanaproget is present in the composition at about 25% wt/wt based upon the total weight of the unit dose.

The composition of the invention also contains microcrystalline cellulose (MCC). In one embodiment, the MCC amounts to about 65% to about 97% wt/wt, or about 65% to about 90% wt/wt of the composition. In one example, the composition includes about 65% wt/wt of MCC. In a further example, the composition includes about 85% wt/wt of MCC.

In another example, the composition includes about 89% wt/wt of MCC. In still a further example, the composition includes about 90% wt/wt of MCC. In yet another example, the composition includes about 97% wt/wt of MCC.

The composition of the invention further includes magnesium stearate and in one embodiment is present at about 0.25% wt/wt of the composition.

Croscarmellose sodium is also present in the composition of the invention and in one embodiment is present at about 2 to about 7% wt/wt of the composition. In one example, the composition includes about 2.4% wt/wt of croscarmellose sodium. In another example, the composition includes about 6% wt/wt of croscarmellose sodium.

A further component of the composition is sodium lauryl sulfate, which is present in one embodiment at about 0.1 to about 3% wt/wt of the composition. In one example, sodium lauryl sulfate is present at about 2% wt/wt of the composition. In another example, sodium lauryl sulfate is present at about 0.2% of the composition.

Still another component of the composition includes povidone, which is present in one embodiment at about 0.1 to about 2% wt/wt of the composition. In one example, povidone is present at about 1.5% wt/wt of the composition. In another example, povidone is present at about 0.16% wt/wt of the composition.

Butylated hydroxyanisole is an optional component of the composition of the invention and in one embodiment amounts to about 0.10% wt/wt, or about 0.1% wt/wt, of the composition.

Without limitation as to the method of preparation of a composition of the invention, an example of a suitable micronized tanaproget composition is provided in Table 1.

TABLE 1

| Component | % wt/wt |
| --- | --- |
| Tanaproget, Micronized | 0.01 |
| Microcrystalline Cellulose | 96.95 |
| Croscarmellose Sodium | 2.42 |
| Sodium Lauryl Sulfate | 0.21 |
| Povidone | 0.16 |
| Magnesium Stearate | 0.25 |

A further example of a suitable micronized tanaproget composition is provided in Table 2.

TABLE 2

| Component | % wt/wt |
| --- | --- |
| Tanaproget, Micronized | 0.10 |
| Microcrystalline Cellulose | 90.15 |
| Croscaimellose Sodium | 6.00 |
| Sodium Lauryl Sulfate | 2.0 |
| Povidone | 1.5 |
| Magnesium Stearate | 0.25 |

Another example of a suitable micronized tanaproget composition is provided in Table 3.

TABLE 3

| Component | % wt/wt |
| --- | --- |
| Tanaproget, Micronized | 0.1 |
| Microcrystalline Cellulose | 90.05 |
| Croscarmellose Sodium | 6.0 |
| Sodium Lauryl Sulfate | 2.0 |
| Butylated Hydroxy Anisole | 0.10 |

TABLE 3-continued

| Component | % wt/wt |
|---|---|
| Povidone | 1.5 |
| Magnesium Stearate | 0.25 |

Still a further example of a suitable micronized tanaproget composition is provided in Table 4.

TABLE 4

| Component | % wt/wt |
|---|---|
| Tanaproget, Micronized | 1.0 |
| Microcrystalline Cellulose | 89.15 |
| Croscarmellose Sodium | 6.0 |
| Sodium Lauryl Sulfate | 2.0 |
| Butylated Hydroxy Anisole | 0.10 |
| Povidone | 1.5 |
| Magnesium Stearate | 0.25 |

Yet another example of a suitable micronized tanaproget composition is provided in Table 5.

TABLE 5

| Component | % wt/wt |
|---|---|
| Tanaproget, Micronized | 5.0 |
| Microcrystalline Cellulose | 85.15 |
| Croscarmellose Sodium | 6.0 |
| Sodium Lauryl Sulfate | 2.0 |
| Butylated Hydroxy Anisole | 0.10 |
| Povidone | 1.5 |
| Magnesium Stearate | 0.25 |

Still another example of a suitable micronized tanaproget composition is provided in Table 6.

TABLE 6

| Component | % wt/wt |
|---|---|
| Tanaproget, Micronized | 25.0 |
| Microcrystalline Cellulose | 65.15 |
| Croscannellose Sodium | 6.0 |
| Sodium Lauryl Sulfate | 2.0 |
| Butylated Hydroxy Anisole | 0.10 |
| Povidone | 1.5 |
| Magnesium Stearate | 0.25 |

The compositions of the invention are typically prepared by mixing micronized tanaproget, or a pharmaceutically acceptable salt thereof, microcrystalline cellulose, croscarmellose sodium, sodium lauryl sulfate, povidone, magnesium stearate, and in one embodiment, butylated hydroxyanisole. In one embodiment, the composition is prepared by wet mixing the components therein with water. In a further embodiment, the sodium lauryl sulfate, butylated hydroxyanisole, and povidone are independently or together combined with water prior to use in the method of the invention.

Such compositions can be utilized as described herein or combined with additional excipients such as microcrystalline cellulose, croscarmellose sodium, and/or magnesium stearate, in addition to those excipients described below, for use. The components can also be in extragranular or intragranular forms, as determined by one of skill in the art and as determined by the requirements of the process.

A variety of apparatuses can be utilized to perform the process of the invention and includes bags of small, medium, and large sizes, screens of varying sizes, and blenders, among others.

The process can also include compacting or milling the composition, typically using compactors and mills selected by one of skill in the art. The milling step is typically performed on particles of varying sizes, i.e., large particles, powders, and fine powders to obtain a preferred and more uniform particle size. The milling can include several separating, recycling, and screening steps to obtain the desired particle sizes.

Drying is generally performed using a suitable drying instrument selected by one of skill in the art such as a fluid bed dryer.

In a further embodiment, the compositions are prepared by diluting the compositions with excipients. Useful excipients for dilution include those set forth below and preferably include MCC, croscarmellose sodium, and magnesium stearate.

For example, compositions containing lesser amounts of tanaproget are prepared by diluting compositions containing greater amounts of tanaproget. For example, compositions containing 0.01 mg, 1 mg, or 5 mg of tanaproget can be prepared. In one embodiment, a composition of the invention containing 0.01 mg of tanaproget is prepared by diluting a composition of the invention containing 0.10 mg, 1 mg, 5 mg, or 25 mg of tanaproget. In a further embodiment, a composition of the invention containing 0.01 mg of tanaproget is prepared by diluting a composition containing 0.10 mg. In another embodiment, a composition of the invention containing 1 mg of tanaproget is prepared by diluting a composition containing 5 mg or 25 mg of tanaproget. In yet a further embodiment, a composition of the invention containing 5 mg tanaproget is prepared by diluting a composition containing 25 mg of tanaproget. In one embodiment, the compositions of the invention prepared by diluting compositions containing higher amounts of tanaproget are diluted with MCC, croscarmellose sodium, and magnesium stearate.

The compositions prepared according to these routes can be encapsulated in a capsule or compressed into a tablet or caplet, which can optionally be encapsulated in a capsule. In one embodiment, the capsule is a hydroxypropyl methylcellulose (hypromellose) capsule.

When compressed into a tablet or caplet, one of skill in the art would readily be able to select a suitable tablet press for use. However, one example of such a press includes the Stokes® B2 Tablet Press, among others.

In one embodiment, a tablet prepared is encapsulated in a capsule. In a further embodiment, the capsule is a hydroxypropyl methylcellulose (hypromellose) capsule. The capsule can be optionally sealed with the tablet therein or a filler can be added to the capsule containing tablet. In one embodiment, the filler includes MCC, croscarmellose sodium, and magnesium stearate. In another embodiment, the tablet is placed in the capsule prior to adding the filler.

If the composition is compressed into a tablet or caplet, the tablets or caplets can optionally be film-coated. Suitable film-coatings are known to those of skill in the art. For example, the film-coating can be selected from among suitable polymers such as hydroxypropylmethylcellulose, ethyl cellulose, polyvinyl alcohol, and combinations thereof. Other suitable film-coatings can be readily selected by one of skill in the art. In one embodiment, the tablet or caplet is coated with an Opadry® seal coat. Where applied, the weight percent of the film coat is generally in the range of 2% wt/wt to 6% wt/wt of the tablet or caplet.

The tablets, caplets, capsules, or tablets-in-capsules containing the composition release about 86 to about 99% of tanaproget after about 90 minutes. In a further embodiment, 85% of the tanaproget, or about 90%, is released in about 15 minutes.

In one embodiment, the compositions contain particles of an optimal size to permit dissolution of the composition, and in a further embodiment, the particles are less than or equal to about 125 µm, or in still a further embodiment are less than 125 µm. The sizes of the particles of the composition are typically measured by passing the solid composition through screens of varying sizes. In one embodiment, about 1% of the particles are greater than or equal to about 150 µm; about 19% of the particles are greater than or equal to about 74 µm; and about 65% of the particles are greater than or equal to about 44 µm. In another embodiment, about 1% of the particles are greater than or equal to about 350 µm; about 1.7% of the particles are greater than or equal to about 180 µm; about 2% of the particles are greater than or equal to about 150 µm; about 21% of the particles are greater than or equal to about 75 µm; and about 66% of the particles are greater than or equal to about 45 µm. In a further embodiment, about 9% of the particles are greater than or equal to about 350 µm; about 17% of the particles are greater than or equal to about 180 µm; about 20% of the particles are greater than or equal to about 150 µm; about 60% of the particles are greater than or equal to about 75 µm; and about 90% of the particles are greater than or equal to about 45 µm. In still another embodiment, about 21% of the particles are greater than or equal to about 350 µm; about 64% of the particles are greater than or equal to about 180 µm; about 74% of the particles are greater than or equal to about 150 µm; about 87% of the particles are greater than or equal to about 75 µm; and about 8% of the particles are greater than or equal to about 45 µm.

If the particles of the compositions are larger than the optimal size and if the same have not yet been encapsulated in a capsule, the same can be subject to further milling and screening steps, among others, to reduce the particle size.

If the composition is already encapsulated in a capsule, the composition can be manually removed from the capsule and subjected to further milling and screening steps to reduce the particle sizes of the composition. In a further embodiment, the capsules containing the composition can be severed using one or more blades or knives, the composition isolated, and the composition subjected to further milling and screening steps to reduce the particle sizes of the composition. Once the optimal particles size has been obtained, the composition is re-encapsulated in a capsule for use.

B. Stability of the Compositions

The compositions are stable over a period of about 1 month for samples stored at varying temperatures and humidities. The term stable as used herein refers to the compositions of the invention which degrade less than about 4%. Typically, it is the tanaproget that degrades in the composition. In one embodiment, the composition is stable at about 20° C./50% relative humidity to about 45° C./75% relative humidity. In one embodiment, the compositions of the invention degrade less than about 4% over a period of greater than 1 month at temperatures of about 25° C. and a relative humidity at or greater than about 60%.

In one embodiment, the compositions of the invention were stored at reduced temperatures, and in a further embodiment, at temperatures of about 5° C. It is desirable that the compositions be stored in the absence of water, air, and moisture.

C. Additional Components of the Compositions of the Invention

Other suitable components can be added to the compositions, provided that the same is not already present, and will be readily apparent to one of skill in the art. Typically, the additional components are inert and do not interfere with the function of the required components of the compositions. The compositions can thereby further include other adjuvants, syrups, elixirs, diluents, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, povidone, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl fumarate, among others. In one embodiment, the lubricant is magnesium stearate.

Granulating agents can include, without limitation, silicon dioxide, starch, calcium carbonate, pectin, crospovidone, and polyplasdone, among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing tanaproget to about 4 to about 6. In one embodiment, the pH of a solution containing tanaproget is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used in the composition include mannitol, calcium phosphate, pregelatinized starch, or sucrose.

D. Methods of Using the Compositions

The invention further provides a method of delivering tanaproget to a patient, where the method includes administering a micronized tanaproget dosing unit according to the invention.

The dosage requirements of tanaproget may vary based on the severity of the symptoms presented and the particular subject being treated. Treatment can be initiated with small dosages less than the optimum dose of tanaproget. Thereafter the dosage is increased until the optimum effect under the circumstances is reached. Precise dosages will be determined by the administering physician based on experience with the individual subject treated. In general, the compositions of this invention are most desirably administered at a concentration that will generally afford effective results without causing any unacceptable harmful or deleterious side effects. For example, an effective amount of micronized tanaproget is generally, e.g., about 0.05 mg to about 1 mg, about 0.05 mg to about 0.3 mg, about 0.05 mg, about 0.075 mg, about 0.1 mg, about 0.15 mg, about 0.2 mg, or about 0.3 mg.

These compositions containing micronized tanaproget are therefore useful in contraception and hormone replacement therapy. The compositions are also useful in contraception and the treatment and/or prevention of, uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors, and in the preparation of medicaments useful therefor. Additional uses of the compositions include stimulation of food intake.

The compositions of the invention are formed into a suitable dosing unit for delivery to a patient. Suitable dosing units include oral dosing units, such as a directly compressible tablets, caplets, capsules, powders, suspensions, microcapsules, dispersible powders, granules, suspensions, syrups, elixirs, and aerosols. In one embodiment, the compositions are compressed into a tablet or caplet, which is optionally added to a capsule, or the compositions are added directly to a capsule. The compositions of the invention can also be formulated for delivery by other suitable routes. These dosing units are readily prepared using the methods described herein and those known to those of skill in the art.

Solid forms, including tablets, caplets, and capsules containing micronized tanaproget can be formed by dry blending tanaproget with the components described above. In one embodiment, the capsules utilized include hydroxypropyl methylcellulose (hypromellose) capsule, or a hard shell gelatin capsule. In another embodiment, the tablets or caplets that contain tanaproget are film-coated. Suitable film-coatings are known to those of skill in the art. For example, the film-coating can be selected from among polymers such as hydroxypropylmethylcellulose, ethyl cellulose, polyvinyl alcohol, and combinations thereof.

A pharmaceutically effective amount of tanaproget can vary depending on the components of the composition, mode of delivery, severity of the condition being treated, the patient's age and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. Daily dosages can also be lowered or raised based on the periodic delivery.

It is contemplated that when the compositions of this invention are used for contraception or hormone replacement therapy, they can be administered in conjunction with one or more other progesterone receptor agonists, estrogen receptor agonists, progesterone receptor antagonists, and selective estrogen receptor modulators, among others.

When utilized for treating neoplastic disease, carcinomas, and adenocarcinomas, they can be administered in conjunction with one or more chemotherapeutic agents, which can readily be selected by one of skill in the art.

E. Kits

Kits or packages containing micronized tanaproget are provided. Kits can include tanaproget and a carrier suitable for administration to a mammalian subject as discussed above. In one embodiment, the tablets, caplets, or capsules are packaged in blister packs, and in a further embodiment in Ultrx™ 2000 blister packs.

The kits or packages containing the compositions are designed for use in the regimens described herein. In one embodiment, these kits are designed for daily oral delivery over 21-day, 28-day, 30-day, or 31-day cycles, among others, or for one oral delivery per day. When the compositions are to be delivered continuously, a package or kit can include the composition in each tablet or caplet. When the compositions of are to be delivered with periodic discontinuation, a package or kit can include placebos on those days when the composition is not delivered.

Additional components may be co-administered with the compositions of the invention and include progestational agents, estrogens, and selective estrogen receptor modulators.

In one embodiment, the kits are also preferably organized to indicate a single oral formulation or combination of oral formulations to be taken on each day of the cycle, in a further embodiment including oral tablets or caplets to be taken on each of the days specified, and in still a further embodiment one oral tablet or caplet will contain each of the combined daily dosages indicated.

In one embodiment, a kit can include a single phase of a daily dosage of the composition of the invention over a 21-day, 28-day, 30-day, or 31-day cycle. Alternatively, a kit can include a single phase of a daily dosage of the composition of the invention over the first 21 days of a 28-day, 30-day, or 31-day cycle. A kit can also include a single phase of a daily dosage of the composition of the invention over the first 28 days of a 30-day or 31-day cycle.

In a further embodiment, a kit can include a single combined phase of a daily dosage of the composition of the invention and a progestational agent over a 21-day, 28-day, 30-day, or 31-day cycle. Alternatively, a kit can include a single combined phase of a daily dosage of the composition of the invention and a progestational agent over the first 21 days of a 28-day, 30-day, or 31-day cycle. A kit can also include a single combined phase of a daily dosage of the composition of the invention and a progestational agent over the first 28 days of a 30-day or 31-day cycle.

In another embodiment, a 28-day kit can include a first phase of from 14 to 28 daily dosage units of the composition of the invention; a second phase of from 1 to 11 daily dosage units of a progestational agent; and, optionally, a third phase of an orally and pharmaceutically acceptable placebo for the remaining days of the cycle.

In yet a further embodiment, a 28-day kit can include a first phase of from 14 to 21 daily dosage units of the composition of the invention; a second phase of from 1 to 11 daily dosage units of a progestational agent; and, optionally, a third phase of an orally and pharmaceutically acceptable placebo for the remaining days of the cycle.

In another embodiment, a 28-day kit can include a first phase of from 18 to 21 daily dosage units of the composition of the invention; a second phase of from 1 to 7 daily dose units of a progestational agent; and, optionally, an orally and pharmaceutically acceptable placebo for each of the remaining 0 to 9 days in the 28-day cycle.

In yet a further embodiment, a 28-day kit can include a first phase of 21 daily dosage units of the composition of the invention; a second phase of 3 daily dosage units for days 22 to 24 of a progestational agent; and, optionally, a third phase of 4 daily units of an orally and pharmaceutically acceptable placebo for each of days 25 to 28.

In another embodiment, a 28-day kit can include a first phase of from 14 to 21 daily dosage units of a progestational agent equal in progestational activity to about 35 to about 150 μg levonorgestrel, a second phase of from 1 to 11 daily dosage units of the composition of the invention; and optionally, a third phase of an orally and pharmaceutically acceptable placebo for the remaining days of the cycle in which no antiprogestin, progestin or estrogen is administered.

In a further embodiment, a 28-day kit can include a first phase of from 14 to 21 daily dosage units of a progestational agent equal in progestational activity to about 35 to about 100 μg levonorgestrel; a second phase of from 1 to 11 daily dosage units of the composition of the invention; and optionally, a third phase of an orally and pharmaceutically acceptable placebo for the remaining days of the cycle in which no antiprogestin, progestin or estrogen is administered.

In one embodiment, the daily dosage of tanaproget remains fixed in each particular phase in which it is delivered. In a further embodiment, the daily dose units described are to be delivered in the order described, with the first phase followed in order by the second and third phases. To help facilitate compliance with each regimen, in a further embodiment the kits contain the placebo described for the final days of the cycle.

A number of packages or kits are known in the art for the use in dispensing pharmaceutical agents for oral use. In one embodiment, the package has indicators for each day of the 28-day cycle, and in a further embodiment is a labeled blister package, dial dispenser package, or bottle.

The kit can further contain instructions for administering the tanaproget compositions.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of Micronized Tanaproget

Tanaproget prepared according to US Patent Application Publication No. 2005/0272702, published Dec. 8, 2005, was milled using a U-10 Comil mill and thereby micronized using a MC50 Jetphainia Micronizer with a EZFH-1.4 Feeder. Particle size was tested periodically for a particle size of less than about 15 μm, and desirably less than about 10 μm, being distributed throughout 50% of the sample. The micronized tanaproget was packed in triple poly-bagged fiber drums. A desiccant was inserted between the outermost bags and the atmosphere in the bags replaced with nitrogen gas.

Example 2

Preparation of 0.10 and 1.0 mg Capsules Containing Micronized Tanaproget

This example provides a wet granulation process for producing capsules containing 0.1 mg and 1.0 mg of micronized tanaproget.

SLS and BHA were dissolved in purified water. Povidone was dissolved in purified water. A portion of intragranular microcrystalline cellulose (MCC) was passed through a screen directly into a high shear mixer. Micronized tanaproget was geometrically pre-blended with a portion of the intragranular MCC and the pre-blend was passed through a screen directly into the high shear mixer. The remaining intragranular MCC and intragranular croscarmellose sodium was passed through a screen directly into the high shear mixer. The composition containing the tanaproget, MCC, and croscarmellose sodium was mixed using the SLS/BHA solution and povidone solution, followed with purified water. Additional purified water was utilized to reach the granulation end-point. Once the granulation end-point was reached, the granulation was dried and passed through a screen. Extragranular MCC and extragranular croscarmellose sodium was passed through a screen and blended with the dried granulation in a blender. Magnesium stearate was passed through a screen and pre-mixed with a portion of the material containing the extragranular MCC, extragranular croscarmellose, and dried granulation. The pre-mix was mixed with the remaining portion of the material containing the extragranular MCC, extragranular croscarmellose, and dried granulation to form the final blend. The final blend was then encapsulated in a #4 hard gel capsule (HGC) to target fill weight of 100 mg. The filled capsules were stored in a poly-lined drum under refrigeration in the absence of light and moisture.

Example 3

Preparation of 0.01 mg Capsule Containing Tanaproget

This example provides a wet granulation process for producing capsules containing 0.01 mg of tanaproget.

The final mix from Example 2 containing 0.10 mg of tanaproget was combined with microcrystalline cellulose, croscarmellose, and magnesium stearate and was encapsulated in a #4 HGC capsule to a target fill weight of 100 mg. See, Table 7. The filled capsules were stored in a poly-lined drum under refrigeration in the absence of light and moisture.

TABLE 7

| Component | % wt/wt | Amount (mg) |
|---|---|---|
| 0.1 mg Granulation of Example 2 | 10.63 | 10.63 |
| MCC | 87.368 | 87.368 |
| Croscarmellose sodium | 1.78 | 1.78 |
| Magnesium Stearate | 0.2228 | 0.2228 |

Example 4

Preparation of 5 and 25 mg Capsules Containing Tanaproget

This example provides a wet granulation process for producing capsules containing 5 mg and 25 mg of tanaproget.

SLS and BHA were dissolved in purified water. Povidone was dissolved in purified water. Micronized tanaproget, intragranular MCC, and intragranular croscarmellose sodium was passed through a screen and mixed in a high shear mixer. The blend containing tanaproget, intragranular MCC, and intragranular croscarmellose sodium was mixed using the SLS/BHA solution, povidone solution, and purified water. If needed, additional purified water was utilized to reach granulation end point. The wet blend was dried and passed through a screen. Extragranular MCC and extragranular croscarmellose sodium were passed through a screen and mixed in a blender with the dried, screened blend.

Magnesium stearate was passed through a screen. The magnesium stearate was pre-mixed with a portion of the composition containing extragranular MCC, extragranular croscarmellose sodium, and tanaproget to form a premix. The premix was then added to the remaining portion of the containing extragranular MCC, extragranular croscarmellose sodium, and tanaproget, and mixed in a blender to foul, a final blend. The final blend was encapsulated in a #4 HGC capsule to target fill weight of 100 mg. The capsules were stored in a poly-lined drum under refrigeration, in the absence of light and moisture.

Example 5

Preparation of 5 and 25 mg Capsules Containing Tanaproget with Reduced Particle Sizes This example provides a process for reducing the particle size of the composition prepared and encapsulated in Example 4.

The capsules from example 4 were passed through a Fitzmil Model D6, with the knives forward at a medium speed (2482 revolutions per minute (RPM)) with a 2 Å mesh screen. This blend was passed through a 20-mesh hand screen to remove the gelatin fragments. The collected blend was then passed through a Fitzmil, using one 50 mesh screen at a high speed (about 4680 RPM) with the hammers forward. The hammered solid was passed through a 60-mesh hand screen, blended in a bag for 2 minutes, and encapsulated in a #4 HGC capsule to a target fill weight of 100 mg. The capsules were stored in a poly-lined drum under refrigeration, in the absence of light and moisture.

Example 6

Preparation of 5 and 25 mg Capsules Containing Tanaproget with Reduced Particle Sizes This example provides a process for reducing the particle size of the composition prepared and encapsulated in Example 4.

The composition contained in the capsules of example 4 was collected by manually emptying the capsules. The collected composition was hand milled using a mortar and pestle and then passed through a Rotap equipped with a 100, 200, and 325 mesh screen and a pan. The hand millings and screening was performed until the solid was sieved. The composition was then bag blend to homogenize the granulation. The blended composition was then encapsulated in a #4 HGC capsule to a target fill weight of 100 mg. The capsules were stored in a poly-lined drum under refrigeration, in the absence of light and moisture.

All documents listed in this specification and priority applications, i.e., U.S. Provisional Patent Application No. 60/675,599, filed Apr. 28, 2005, and U.S. patent application Ser. No. 11/412,014, filed Apr. 26, 2006, are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A method of treating endometriosis, said method comprising administering a composition to a patient in need thereof, said composition comprising:
    (i) about 0.01 to about 25 mg of tanaproget, or a tautomer or pharmaceutically acceptable salt thereof,
    (ii) about 65% to about 97% wt/wt of microcrystalline cellulose,
    (iii) about 2 to about 7% wt/wt of croscarmellose sodium,
    (iv) about 2% wt/wt of sodium lauryl sulfate,
    (v) about 0.1 to about 2% wt/wt of povidone,
    (vi) about 0.25% wt/wt of magnesium stearate, and
    (vii) about 0.10% wt/wt of butylated hydroxyanisole.

2. A method of treating endometriosis, said method comprising administering a composition to a patient in need thereof, said composition comprising:
    (i) about 0.05 to about 1 mg of tanaproget, or a tautomer or pharmaceutically acceptable salt thereof,
    (ii) about 65% to about 97% wt/wt of microcrystalline cellulose,
    (iii) about 2 to about 7% wt/wt of croscarmellose sodium,
    (iv) about 2% wt/wt of sodium lauryl sulfate,
    (v) about 0.1 to about 2% wt/wt of povidone,
    (vi) about 0.25% wt/wt of magnesium stearate, and
    (vii) about 0.10% wt/wt of butylated hydroxyanisole.

3. The method according to claim 2, said composition comprising about 0.05 to about 0.3 mg of tanaproget.

4. The method according to claim 2, said composition comprising about 0.05 mg of tanaproget.

5. The method according to claim 2, said composition comprising about 0.075 mg of tanaproget.

6. The method according to claim 2, said composition comprising about 0.1 mg of tanaproget.

7. The method according to claim 2, said composition comprising about 0.15 mg of tanaproget.

8. The method according to claim 2, said composition comprising about 0.2 mg of tanaproget.

9. The method according to claim 2, said composition comprising about 0.3 mg of tanaproget.

10. A method of treating endometriosis, said method comprising administering a composition to a patient in need thereof, said composition comprising:
    (i) about 0.01% to about 25% wt/wt of micronized tanaproget, or a tautomer or pharmaceutically acceptable salt thereof,
    (ii) about 65% to about 97% wt/wt of microcrystalline cellulose,
    (iii) about 2 to about 7% wt/wt of croscarmellose sodium,
    (iv) about 2% wt/wt of sodium lauryl sulfate,
    (v) about 0.1 to about 2% wt/wt of povidone,
    (vi) about 0.25% wt/wt of magnesium stearate, and
    (vii) about 0.10% wt/wt of butylated hydroxyanisole.

11. The method according to claim 10, said composition further comprising water.

12. The method according to claim 10, said composition comprising about 0.01% wt/wt of tanaproget.

13. The method according to claim 10, said composition comprising about 0.10% wt/wt of tanaproget.

14. The method according to claim 10, said composition comprising about 1% wt/wt of tanaproget.

15. The method according to claim 10, comprising about 5% wt/wt of tanaproget.

16. The method according to claim 10, said composition comprising about 25% wt/wt of tanaproget.

17. The method according to claim 10, wherein the particles of said micronized tanaproget are less than about 10 μm.

18. The method according to claim 10, wherein the particles of said composition are less than, or equal to, about 125 μm.

19. The method according to claim 10, further comprising administering a second progesterone receptor agonist, estrogen receptor agonist, progesterone receptor antagonist, selective estrogen receptor modulator, or combinations thereof.

20. A method of treating uterine myometrial fibroids, benign prostatic hypertrophy, dysfunctional bleeding, uterine leiomyomata, or polycystic ovary syndrome, said method comprising administering a composition of claim 1 to a patient in need thereof, said composition comprising:
   (i) about 0.01% to about 25% wt/wt of micronized tanaproget, or a tautomer or pharmaceutically acceptable salt thereof,
   (ii) about 65% to about 97% wt/wt of microcrystalline cellulose,
   (iii) about 2 to about 7% wt/wt of croscarmellose sodium,
   (iv) about 2% wt/wt of sodium lauryl sulfate,
   (v) about 0.1 to about 2% wt/wt of povidone,
   (vi) about 0.25% wt/wt of magnesium stearate, and
   (vii) about 0.10% wt/wt of butylated hydroxyanisole.

21. The method according to claim 20, said composition further comprising water.

22. The method according to claim 20, said composition comprising about 0.01% wt/wt of tanaproget.

23. The method according to claim 20, said composition comprising about 0.10% wt/wt of tanaproget.

24. The method according to claim 20, said composition comprising about 1% wt/wt of tanaproget.

25. The method according to claim 20, comprising about 5% wt/wt of tanaproget.

26. The method according to claim 20, said composition comprising about 25% wt/wt of tanaproget.

27. The method according to claim 20, wherein the particles of said micronized tanaproget are less than about 10 μm.

28. The method according to claim 20, wherein the particles of said composition are less than, or equal to, about 125 μm.

29. The method according to claim 20, further comprising administering a second progesterone receptor agonist, estrogen receptor agonist, progesterone receptor antagonist, selective estrogen receptor modulator, or combinations thereof.

* * * * *